(12) United States Patent
Taghizadeh et al.

(10) Patent No.: US 7,402,423 B2
(45) Date of Patent: Jul. 22, 2008

(54) APPARATUS FOR THE DETECTION OF PEPSIN

(75) Inventors: Farhan Taghizadeh, Uniontown, PA (US); Scott Horner, Brighton, NY (US); Kevin Bucholtz, Scottsville, NY (US)

(73) Assignee: Biomed Solutions, LLC, Pittsford, NY (US)

( * ) Notice: Subject to any disclaimer, the term of this patent is extended or adjusted under 35 U.S.C. 154(b) by 0 days.

(21) Appl. No.: 10/918,562

(22) Filed: Aug. 13, 2004

(65) Prior Publication Data

US 2006/0035307 A1   Feb. 16, 2006

(51) Int. Cl.
*C12M 1/34* (2006.01)

(52) U.S. Cl. ...................... 435/287.1; 435/24

(58) Field of Classification Search ............ 435/24
See application file for complete search history.

(56) References Cited

U.S. PATENT DOCUMENTS

| | | | |
|---|---|---|---|
| 4,168,703 A | | 9/1979 | Kenigsberg |
| 4,384,041 A * | | 5/1983 | Matsumoto et al. ............ 435/24 |
| 4,455,381 A | | 6/1984 | Magnusson |
| 4,503,859 A | | 3/1985 | Petty |
| 4,702,260 A | | 10/1987 | Wang |
| 4,748,114 A | | 5/1988 | Kallies |
| 4,795,421 A | | 1/1989 | Blasius, Jr. |
| 4,880,015 A | | 11/1989 | Nierman |
| 4,962,024 A * | | 10/1990 | Schulte ........................ 435/14 |
| 5,056,521 A | | 10/1991 | Parsons |
| 5,117,827 A | | 6/1992 | Stuebe |
| 5,254,591 A | | 10/1993 | Martin |
| 5,372,126 A | | 12/1994 | Blau |
| 5,524,622 A | | 6/1996 | Wilson |
| 5,571,116 A | | 11/1996 | Bolanos |
| 5,738,110 A | | 4/1998 | Beal |
| 5,797,693 A | | 8/1998 | Jaeger |
| 5,879,897 A * | | 3/1999 | Koufman .................... 435/7.4 |
| 5,951,468 A | | 9/1999 | Orr |
| 5,975,897 A | | 11/1999 | Propp |
| 6,180,063 B1 | | 1/2001 | Markart |
| 6,238,335 B1 | | 5/2001 | Silverman |
| 6,315,951 B1 | | 11/2001 | Markart |
| 6,338,345 B1 | | 1/2002 | Johnson |
| 6,407,206 B1 * | | 6/2002 | Hayashi et al. ............. 530/329 |
| 6,441,131 B1 * | | 8/2002 | Hayashi et al. ............. 530/300 |
| 6,441,898 B1 | | 8/2002 | Markart |
| 6,458,596 B1 | | 10/2002 | Poellmann |
| 6,475,145 B1 | | 11/2002 | Baylor |
| 6,514,460 B1 | | 2/2003 | Fendrock |
| 6,514,461 B1 | | 2/2003 | Lappe |
| 6,525,549 B1 | | 2/2003 | Poellmann |
| 6,548,266 B1 * | | 4/2003 | Zhang et al. .................. 435/15 |
| 6,689,320 B1 | | 2/2004 | Markart |
| 6,716,393 B2 | | 4/2004 | Lappe |
| 6,725,866 B2 | | 4/2004 | Johnson |
| 2004/0002168 A1 * | | 1/2004 | Remington et al. ......... 436/518 |
| 2004/0029205 A1 | | 2/2004 | Small |

OTHER PUBLICATIONS

Orlando, Roy C.; Pathogenesis of Gastroesophageal Reflux Disease; The American Journal of the Medical Sciences, vol. 326, No. 5, Nov. 2003, pp. 274-278.

Napierkowski, John, et al.; Extraesophageal Manifestations of GERD; The American Journal of the Medical Sciences, vol. 326, No. 5, Nov. 2003, pp. 285-299.

Kourman, James A.; The Otolaryngologic Manifestations of . . . ; The Laryngoscope, vol. 101, No. 4, Pt 2, Apr. 1991, pp. 1-78.

White, David R. et al.; Gastroesophageal Reflux and Eustachian . . . ; The Laryngoscope; vol. 112, No. 6, Jun. 2002, p. 955-961.

Matthews Brian L.; Reflux in Infants with Laryngomalacia; Otolaryngology, vol. 120 No. 6; Jun. 1999, pp. 860-864.

Potluri, Sunitha, et al.; Comparison of a Salivary/Sputum Pepsin Assay with . . . ; Digestive Diseases and Sciences, vol. 48, No. 9; Sep. 2003; pp. 1813-1817.

Sontag, SJ; Gastroesophageal Reflux Disease and its consequences; Journal of the Association for Academic Minority Physicians; vol. 3, No. 4, Oct. 1992; pp. 130-136.

Potlouri, S. et al.; Comparison of a Salivary/Sputum Pepsin Assay with 24-Hour Esophageal pH Monitoring for Detection of Gastric Reflux into the Proximal Esophagus, Oropharynx, and Lung; Dig. Dis. Sci., Sep. 2003, pp. 1813-1817, vol. 48 No. 9.

* cited by examiner

*Primary Examiner*—Ralph Gitomer
(74) *Attorney, Agent, or Firm*—Proteus Patent Practice LLC; Henry E. Auer

(57) ABSTRACT

An apparatus for detecting pepsin comprising a solid support, and a peptide chain wherein the peptide chain is operatively configured to be cleaved by pepsin, and the peptide chain is disposed on a surface of the solid support.

44 Claims, 7 Drawing Sheets

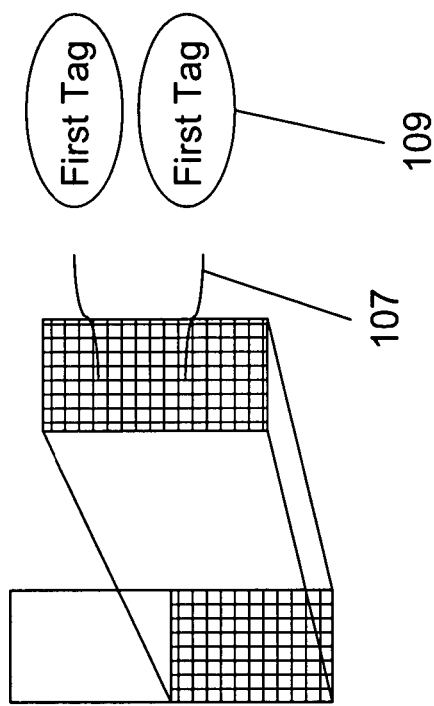
FIG. 1B
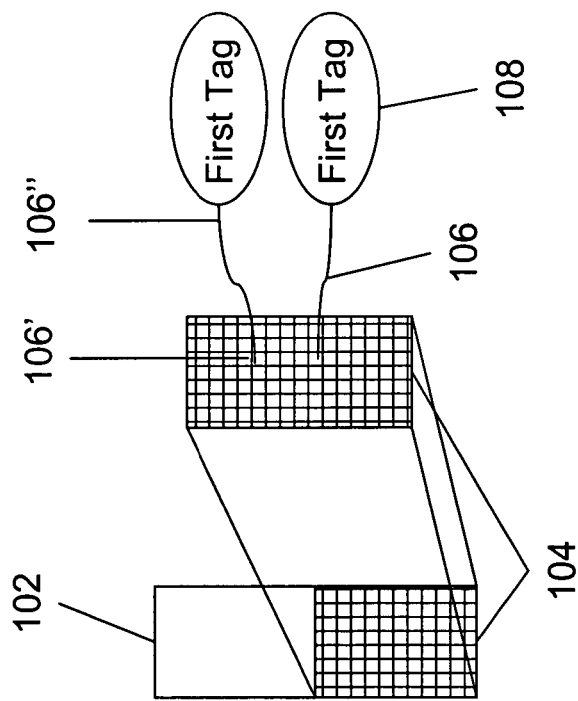
FIG. 1A
FIG. 1

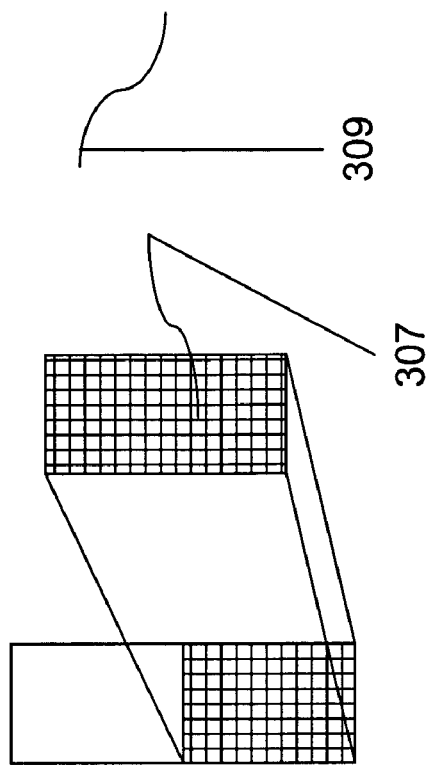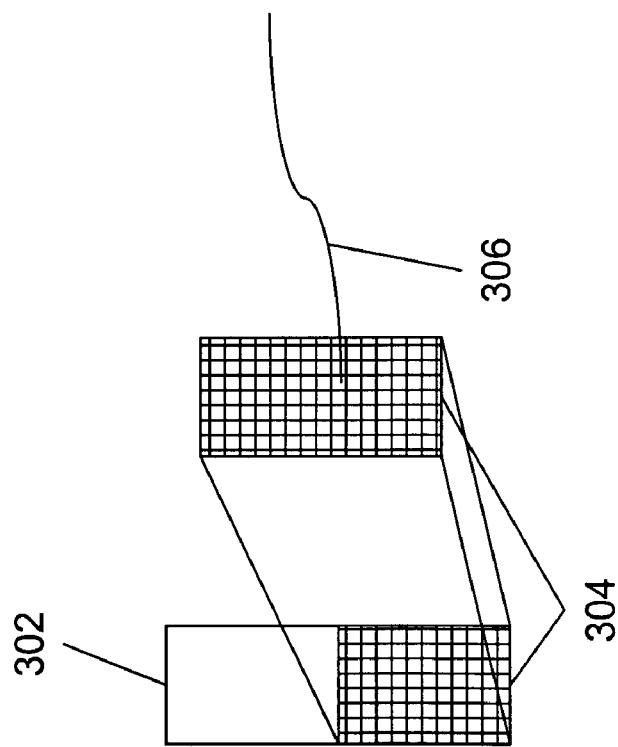
FIG. 3

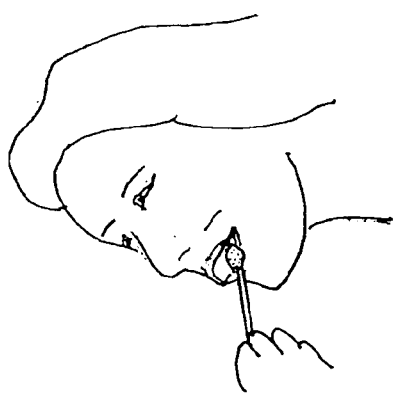
FIG. 7B
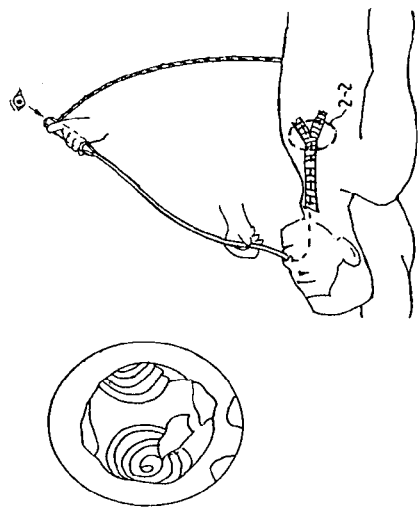
FIG. 7A
FIG. 7C
FIG. 7

APPARATUS FOR THE DETECTION OF PEPSIN

FIELD OF THE INVENTION

This invention relates, in one embodiment, to medical diagnostic testing, and more particularly to a medical test useful for the detection of enzymes, and in particular pepsin.

BACKGROUND OF THE INVENTION

Gastroesophageal reflux disease (GERD) represents a host of symptoms and pathologies believed to result from the inappropriate exposure of the esophagus and upper airway to gastric acid. A wide host of diseases are attributed to this exposure, ranging from esophageal injury to the wide host of disorders termed "laryngopharyngeal reflux".

As is disclosed in U.S. Pat. No. 6,725,866; "Current methods to treat gastroesophageal reflux disease consist of lifestyle changes such as weight loss, avoidance of certain foods that exacerbate the symptoms of GERD and avoidance of excessive bending. Elevation of the head of the bed helps prevent nocturnal reflux. While these avoidance strategies may be helpful, there is relatively little data supporting the efficacy of lifestyle modification alone for the treatment of GERD. Medications for the treatment of GERD have been administered for years with little or no success." One symptom of GERD mentioned in the above referenced patent is dyspepsia. "Dyspepsia, or heartburn, is defined as a burning sensation or discomfort behind the breastbone or sternum and is the most common symptom of GERD. Other symptoms of GERD include dysphasia, odynophagia, hemorrhage, water brash, and pulmonary manifestations such as asthma, coughing or intermittent wheezing due to acid aspiration. Dyspepsia may also mimic the symptoms of a myocardial infarction or severe angina pectoris." GERD has also been linked to irregularities in the upper airways, such as asthma. It is believed that the low levels of acid released due to GERD are responsible for these irregularities. It is often difficult to properly diagnose GERD, as many other conditions mimic the symptoms of GERD. As is taught in U.S. Pat. No. 5,951,468 "since the symptoms of GERD often mimic cardiac chest pain, the physician must confirm that the symptoms are in fact due to reflux and not to a cardiac condition."

U.S. Pat. No. 4,168,703 teaches an alternative testing conditions involve the monitoring the pressure within the lower esophagus. This testing procedure is deficient due to the substantial degree of patient discomfort involved with this method.

U.S. Pat. Nos. 4,503,859 and 5,117,827 teach a procedure to test for reflux which includes esophageal pH monitoring, with esophageal manometry testing. This testing occurs by passing a catheter into the esophagus, and then monitoring pH and sphincter pressures for 24 hours through the use of an ambulatory monitoring device. Test results are then analyzed to determine reflux degree. Such ambulatory devices are extremely inconvenient for the patient. In addition, these testing conditions require a significant amount of time to obtain a result.

U.S. Pat. No. 5,254,591 discloses a pharmaceutical composition useful for treating gastroesophageal reflux disease. This patent clearly fails to disclose or suggest a method of detection for the disease.

U.S. Pat. No. 5,524,622 teaches a method of detecting increased blood flow to certain regions of the gastrointestinal tract, and thus is able to detect inflammation of the tract. This technique is deficient in that it is significantly more complex and considerably more expensive that that of the instant invention. The equipment needed to conduct such testing is exceedingly specialized.

U.S. Pat. No. 5,571,116 discloses a minimally invasive device and method for the treatment of gastroesophageal reflux disease. The techniques taught in this patent may be used in conjunction with the instant invention. However, this patent fails to disclose a method of detection of gastroesophageal reflux disease.

U.S. Pat. No. 5,738,110 teaches a retrievable capsule useful for obtaining samples of gastroesophegeal fluids. In this manner, epithelial cells may be removed for later testing. While this patent teaches methods of obtaining samples for testing, it fails to teach testing methodology itself.

U.S. Pat. No. 5,879,897 teaches an immunoassay technique for the detection of pepsin. This patent provides " . . . methods of detecting and diagnosing reflux diseases and disorders by detecting the presence of pepsin in airway secretions (e.g. throat, lung, esophagus, or mouth mucus/sputum/saliva) or other bodily fluids of subjects suspected of having a reflux disorder of disease. An advantage of the disclosed methods over methods based on detection of pH changes is that pepsin or pepsinogen from reflux becomes trapped in the mucus and remains in the throat or esophagus longer than acid (hydrogen ions) and can thus be detected for hours or days after a reflux event." The techniques taught in U.S. Pat. No. 5,879,897 can be distinguished from the instant invention by the nature of the detection system itself. The instant invention, in one embodiment, detects the enzymatic activity of pepsin. The aforementioned antibody techniques are deficient in that they detect pepsin itself, even when such pepsin may not be an active enzyme. Additionally, such immunoassay techniques are known to take a significant amount of time to obtain results.

U.S. Pat. No. 5,951,468 discloses a method for testing for esophageal acid sensitivity by attempting to induce the symptoms of gastroesophageal reflux through the ingestion of weak acids. This patent is clearly distinguished from the instant invention by the very nature of the test.

U.S. Pat. No. 6,238,335 teaches a method and device for the treatment of gastroesophageal reflux disease. The techniques taught in this application involve the augmentation of the epithelial lining to promote acid resistance.

U.S. Pat. No. 6,338,345 discloses a device and method for the delivery of treatment agents into the esophagus for the treatment of gastroesophageal reflux disease. Both of these patents fail to teach or suggest a method of testing for gastroesophageal reflux disease.

U.S. Pat. No. 6,475,145 teaches a method for monitoring pH levels over a prolonged period of time. The techniques of this patent are deficient in that they fail to teach or suggest a rapid testing method for the detection of gastroesophageal reflux disease.

U.S. patent application 2004/0002168 discloses a test strip to test for cerebrospinal fluid. This application contains no suggestion or motivation to modify this test strip to test for pepsin. Other test strips and/or test strip reading devices are disclosed in U.S. Pat. No. 6,180,063 (Measuring Device for Use with a Test Strip); U.S. Pat. No. 6,315,951 (Test Strip Measuring System); U.S. Pat. No. 6,514,460 (Luminous Glucose Monitoring Device); U.S. Pat. Nos. 6,514,461 and 6,716,393 (System for Automatically Testing a Fluid Specimen); U.S. Pat. No. 6,689,320 (Test Strip Measuring System); and the like.

The content of U.S. Pat. Nos. 4,168,703; 4,455,381; 4,503,859; 5,117,827; 5,254,591; 5,524,622; 5,571,116; 5,738,110; 5,879,897; 5,951,468; 6,180,063; 6,238,335; 6,315,951;

6,338,345; 6,475,145; 6,514,461; 6,689,320; 6,716,393; 6,725,866 and U.S. patent application 2004/0002168 is hereby incorporated by reference into this specification.

Yet another testing method involves nasogastric intubation of the patient and subsequently adding dilute acid to intentionally trigger the condition to be tested for. As is known to those skilled in the art, this test is often referred to as the "Berstein acid perfusion test."

As acknowledged in U.S. Pat. No. 5,951,468 "Currently, there is no simple diagnostic test or procedure that can be done either in a physician's office or in an individual's home to assist with the diagnosis of acid reflux and GERD."

It is an object of this invention to provide at least one of the following; a method for the detection of an enzyme that is rapid and convenient enough that it can be performed in a physician's office or similar location without the need for ambulatory monitoring devices; a method for detecting an enzyme wherein the enzyme can be detected in less than two hours (i.e. "point of care" detection).

SUMMARY OF THE INVENTION

In accordance with the present invention, there is provided an apparatus for detecting pepsin comprising a solid support, and a peptide chain wherein the peptide chain is operatively configured to be cleaved by pepsin, and the peptide chain is disposed on a surface of the solid support.

BRIEF DESCRIPTION OF THE DRAWINGS

The invention will be described by reference to the following drawings, in which like numerals refer to like elements, and in which:

FIG. 1 is a schematic diagram of one test strip of the invention;

FIG. 1A is a schematic diagram of a test strip with a first tag attached;

FIG. 1B is a schematic diagram of a test strip with the first tag of FIG. 1A released;

FIG. 3 is a schematic diagram of another test strip of the invention;

FIG. 3A is a schematic diagram of a test strip before enzymatic cleavage;

FIG. 3B is a schematic diagram of a test strip after enzymatic cleavage;

FIG. 7 is a schematic diagram of three suitable methods for obtaining samples for use with the instant invention;

FIG. 7A is a schematic diagram of one method of tubation to obtain samples;

FIG. 7B is a schematic diagram of one method of oral swabbing to obtain samples; and FIG. 7C is a schematic diagram of one method of passive sample collection.

Figure 2:
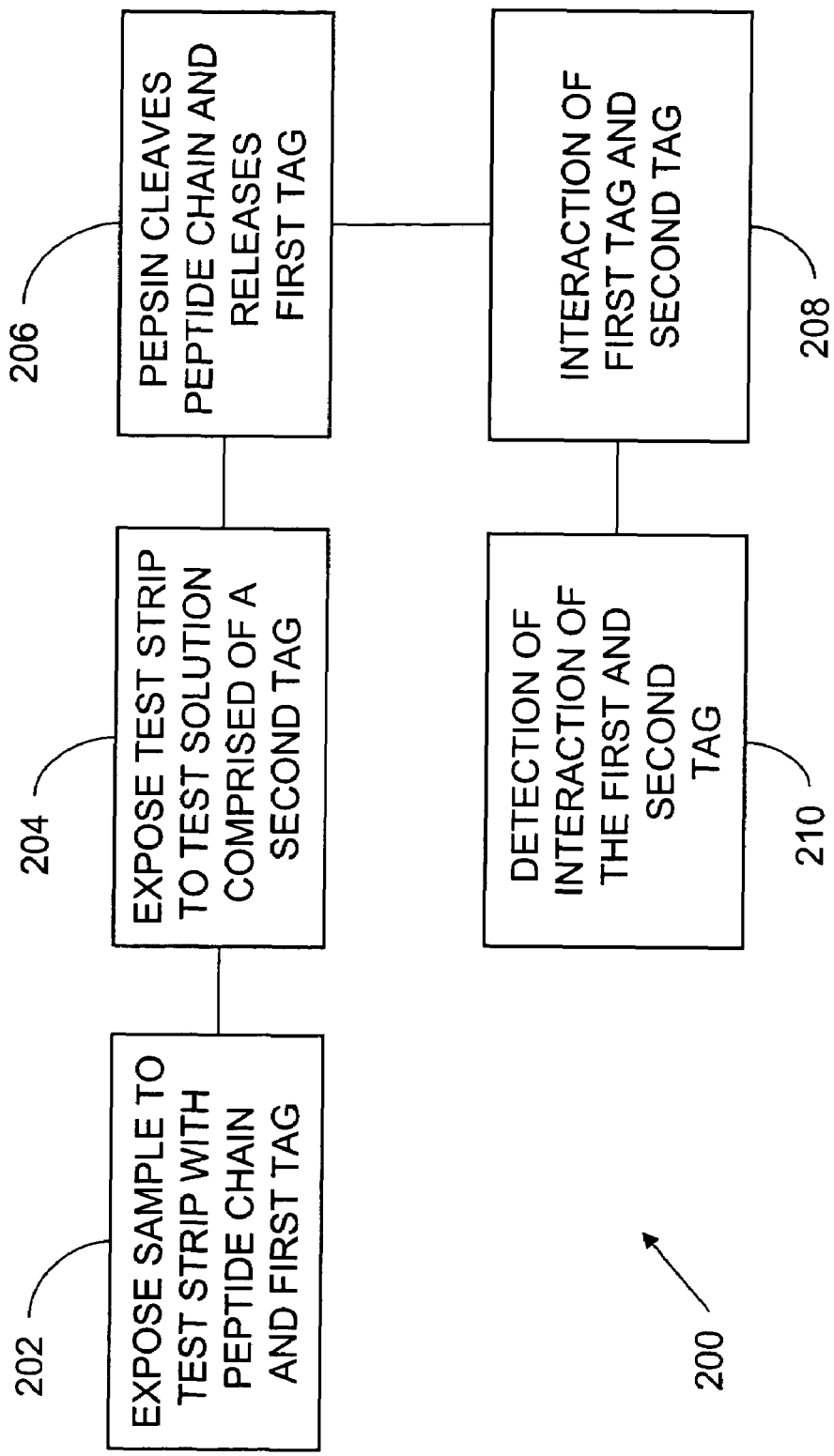
FIG. 2 is a flow diagram of one process of the invention utilizing tags.

The present invention will be described in connection with a preferred embodiment, however, it will be understood that there is no intent to limit the invention to the embodiment described. On the contrary, the intent is to cover all alternatives, modifications, and equivalents as may be included within the spirit and scope of the invention as defined by the appended claims.

DESCRIPTION OF THE PREFERRED EMBODIMENTS

FIG. 1 illustrates one embodiment of the invention wherein pepsin is detected in a sample (for example, in a human saliva sample) using chemical tags. In one embodiment, a test strip 102, a substrate, a solid support, a stationary phase, or other immobilizing agent is used. In the embodiment shown in FIG. 1, test strip 102 is comprised of testing area 104. Disposed on the surface of testing area 104 is a multiplicity of peptide chain 106. In one embodiment, peptide chain 106 contains an aromatic amino acid residue such as phenylalanine, tyrosine, tryptophan, histidine, and the like, which is operatively configured to be cleaved by enzymatic hydrolysis of the peptide bond by pepsin. A first end 106' of peptide chain 106 is attached to the testing area 104. A second end 106" of peptide chain 106 is attached to a first tag 108. Upon enzymatic cleavage of peptide chain 106 by pepsin (forming cleaved peptide chain 107), first tag 108 is released to form released first tag 109. Thus, the concentration of released first tag 109 is diagnostic of the presence of pepsin.

Suitable peptide chains include (from N to C terminus), but are not limited to: -glycine-glycine-glycine-asparagine-X-asparagine-glycine-glycine-glycine - - - TAG where X is an aromatic amino acid (such as, for example, phenylalanine, tyrosine, tryptophan, and the like).

In one embodiment, it is preferred that the amino acid positions flanking the aromatic amino acid X not be valine, alanine or glycine, as the presence of such residues is known to diminish the activity of pepsin. Suitable peptides can be obtained commercially, synthesized on a commercially available peptide synthesizer (in house) or synthesized by hand using standard solid phase chemical techniques.

In one embodiment, the test does not utilize a traditional test strip. Instead, a different solid support or other substrate is used. In one embodiment of the present invention, the peptide or protein (containing our dye or indicator-tag) is covalently attached to the wall of an Eppendorf tube or test tube or other similar container. The resulting solution is then screened (following exposure to the solution that may or may not contain pepsin obtained from the patient) for the release of the tag or dye, indicating the presence of pepsin.

In the embodiment shown in FIG. 2, a testing solution is used to visualize the release of the first tag. In step 202 of the process 200, a sample to be tested is exposed to a test strip. This test strip comprises the aforementioned peptide chain and first tag. If pepsin is present, the then the first tag will be released. In step 204 of the process, the test strip is exposed to a test solution. This test solution comprises a second tag which is operatively configured to interact with the released first tag. In one embodiment, the test solution is a buffered solution designed to promote the enzymatic cleavage of the peptide chain by pepsin (pH 1-3, for optimum pepsin activity). In one embodiment, the test strip is disposed within the test solution for a period of less than about 3 hours, and preferably for less than about 2 hours. In step 206 pepsin cleaves the peptide bond and releases the first tag into the test solution, where it contacts the second tag. Although some degree of cleavage may occur prior to the introduction of the test strip into the test solution, in the embodiment depicted in FIG. 2 most of the cleavage occurs after exposure to the test solution. In step 208 the released first tag interacts with the second tag present in the test solution. This interaction is detectable in a variety of means, depending on the nature of the first and second tags. In one embodiment, the chemical combination of the first and second tag may be detected visually (i.e. a change in coloration of the solution). In another embodiment, the color changes that take place are outside of the visual range of human color perception, and spectroscopic instruments are used to detect the change. In yet another embodiment, the color changes are within the visual spectrum of the human eye, but spectroscopic instruments are used so as to quantify the measurements. Numerous suitable instruments for test strip analysis are known to those skilled in the art. Reference may be had to U.S. Pat. Nos. 4,748,114; 5,797,693; 6,441,898; 6,458,596; 6,525,549; and the like. The content of U.S. Pat. Nos. 4,748,114; 5,797,693; 6,441,898; 6,458,596; and 6,525,549; is hereby incorporated by reference into this specification. Thus it is now feasible to compare the result to a colorimetric gradient and to determine not only the presence of pepsin but also quantify how much is present in a given sample.

FIG. 3 illustrates one embodiment of the invention wherein pepsin is detected in a sample (for example, in a human saliva sample) without using chemical tags. In one embodiment, a test strip 302 or other solid support/immobilizing agent is used. In the embodiment shown in FIG. 3, test strip 302 is comprised of testing area 304. Disposed on the surface of testing area 304 is a multiplicity of peptide chains 306. In one embodiment, peptide chain 306 contains amino acid residues operatively configured to be cleaved by enzymatic hydrolysis of the peptide bond by pepsin. A first end of peptide chain 306 is attached to the testing area 304. Upon enzymatic cleavage of peptide chain 306 by pepsin, two peptide fragments are generated; cleaved peptide chain 307 and released peptide chain 309. This cleavage results in a new exposed terminus of cleaved peptide chain 307. A dye may then be used that stains the chemical functional group that has been exposed on the terminus of cleaved peptide chain 307. Thus, the presence of the functional group on the cleaved peptide chain 307 is diagnostic of the presence of pepsin.

Figure 4:
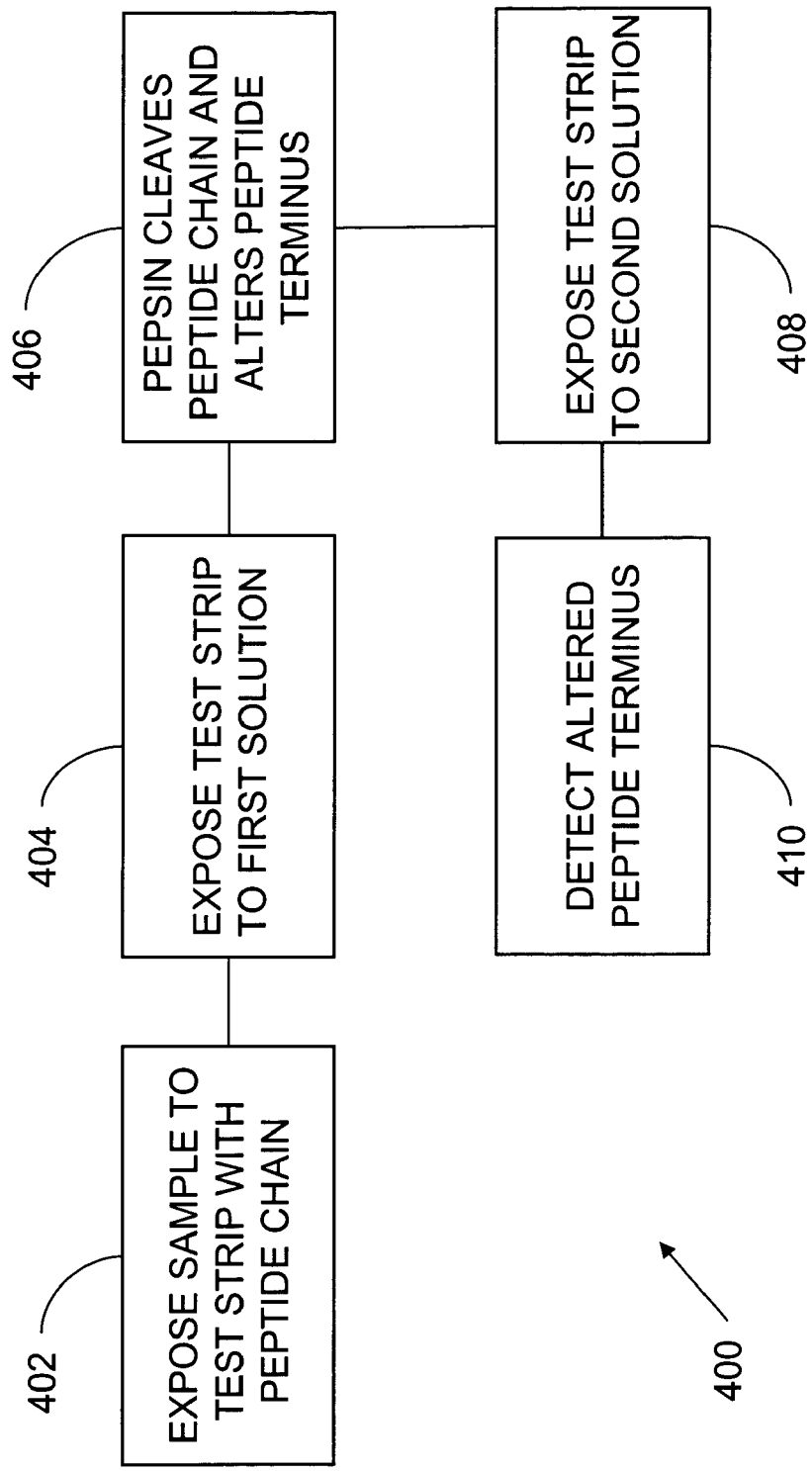
FIG. 4 is a flow diagram of one process of the invention utilizing enzymatic cleavage.

In the embodiment shown in FIG. 4, a series of solutions are used to visualize the alteration of the peptide terminus. In step 402 of the process 400, a sample to be tested is exposed to a test strip. This test strip comprises a peptide chain operatively configured to be cleaved by pepsin. If pepsin is present, then the peptide chain will be cleaved. In step 404 of the process the test strip is exposed to a test solution. In one embodiment, the test solution is a buffered solution designed to promote the enzymatic cleavage of the peptide chain by pepsin (pH 1-3, for optimum pepsin activity). In one embodiment, the test strip is disposed within the test solution for a period of less than about 3 hours, and preferably for less than about 2 hours. In another embodiment, the test strip is disposed within the test solution for a period of less than about 1 hour. In step 406, pepsin cleaves the peptide bond and exposes a new peptide terminus. Although some degree of cleavage may occur prior to the introduction of the test strip into the test solution, in the embodiment depicted in FIG. 4 most of the cleavage occurs after exposure to the test solution. In step 408 the cleaved peptide chain is exposed to conditions that allow for the visualization of the altered terminus. As would be appreciated by those skilled in the art, such staining techniques are well known. By way of illustration and not limitation, one may use a solution of Coomassie Blue stain. Such a solution is known to stain primary amines on peptide chains. Other suitable stains are commonly used on chromatography arts. Spectroscopic techniques similar to those discussed above can be used to detect subtle color changes. Such spectroscopic techniques can also be used to detect spectral changes outside of the visible spectrum.

Figure 5:
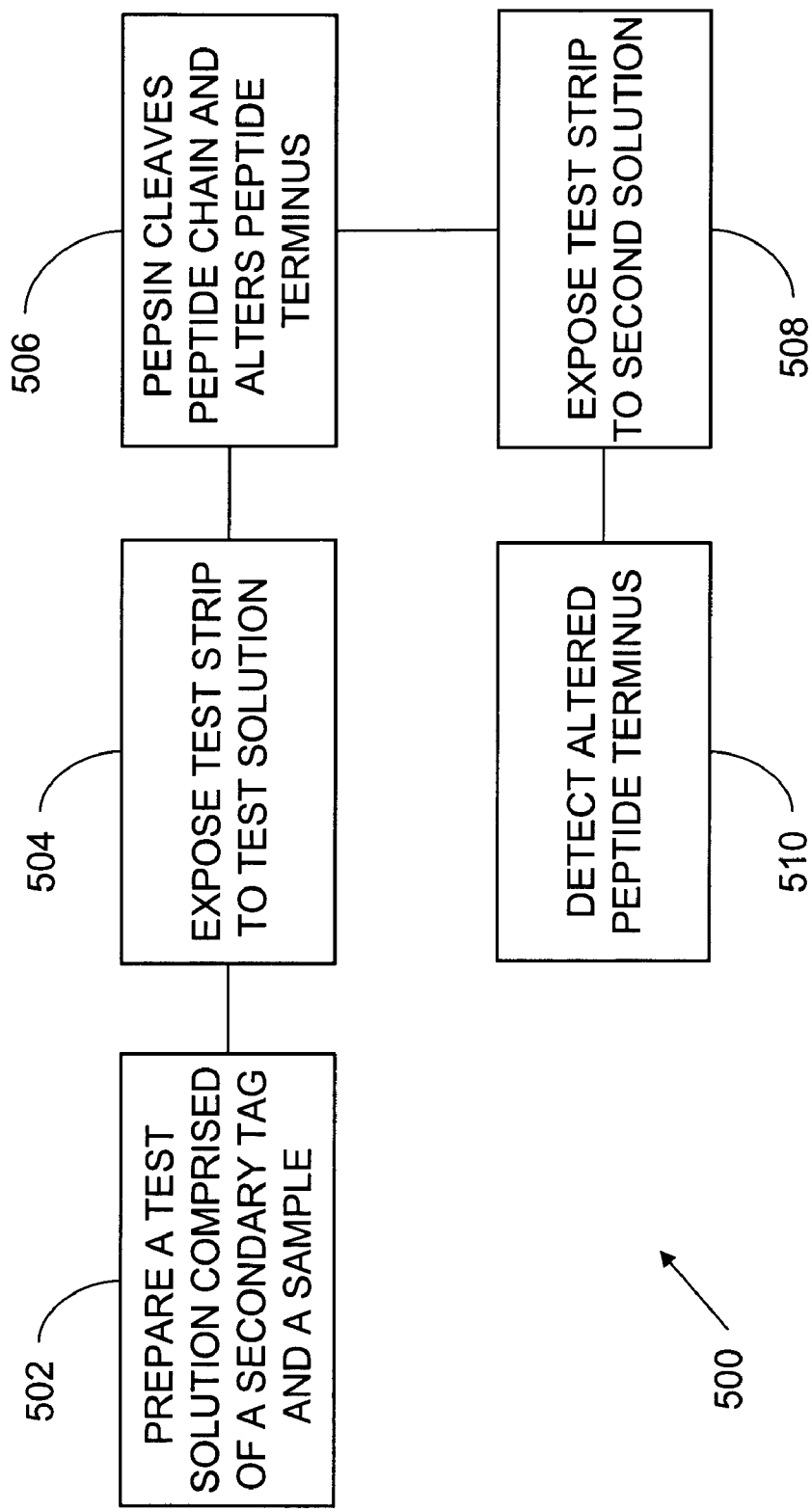
FIG. 5 is a flow diagram of one process of the invention utilizing enzymatic cleavage.

In the embodiment shown in FIG. 5, a series of solutions are used to visualize the alteration of the peptide terminus. The process illustrated in FIG. 5 is similar to that depicted in FIG. 4 except that the sample to be tested is disposed within the solution, and not placed directly on the test strip. In step 502 of the process 500, test solution is prepared. This test solution is comprised of the sample to be tested. In one embodiment, the test solution is further comprised of buffers to enhance the rate of enzymatic cleavage. In one embodiment, the test solution is a buffered solution designed to promote the enzymatic cleavage of the peptide chain by pepsin (pH 1-3, for optimum pepsin activity). In step 504 of the process the test strip is exposed to the test solution. This test strip comprises a peptide chain operatively configured to be cleaved by pepsin. If pepsin is present in the test solution, the then peptide chain will be cleaved. In one embodiment, the test strip is disposed within the test solution for a period of less than about 3 hours, and preferably for less than about 2 hours. In step 506, pepsin cleaves the peptide bond and exposes an altered terminus. Although some degree of cleavage may occur prior to the introduction of the test strip into the test solution, in the embodiment depicted in FIG. 5 most of the cleavage occurs after exposure to the test solution. In step 508 the cleaved peptide chain is exposed to conditions that allow for the visualization of the altered terminus. By way of illustration and not limitation, one may use a solution of Coomassie Blue stain. Such a solution is known to stain primary amines on peptide chains. Spectroscopic techniques similar to those discussed above can be used to detect subtle color changes. Such spectroscopic techniques can also be used to detect spectral changes outside of the visible spectrum.

Figure 6:
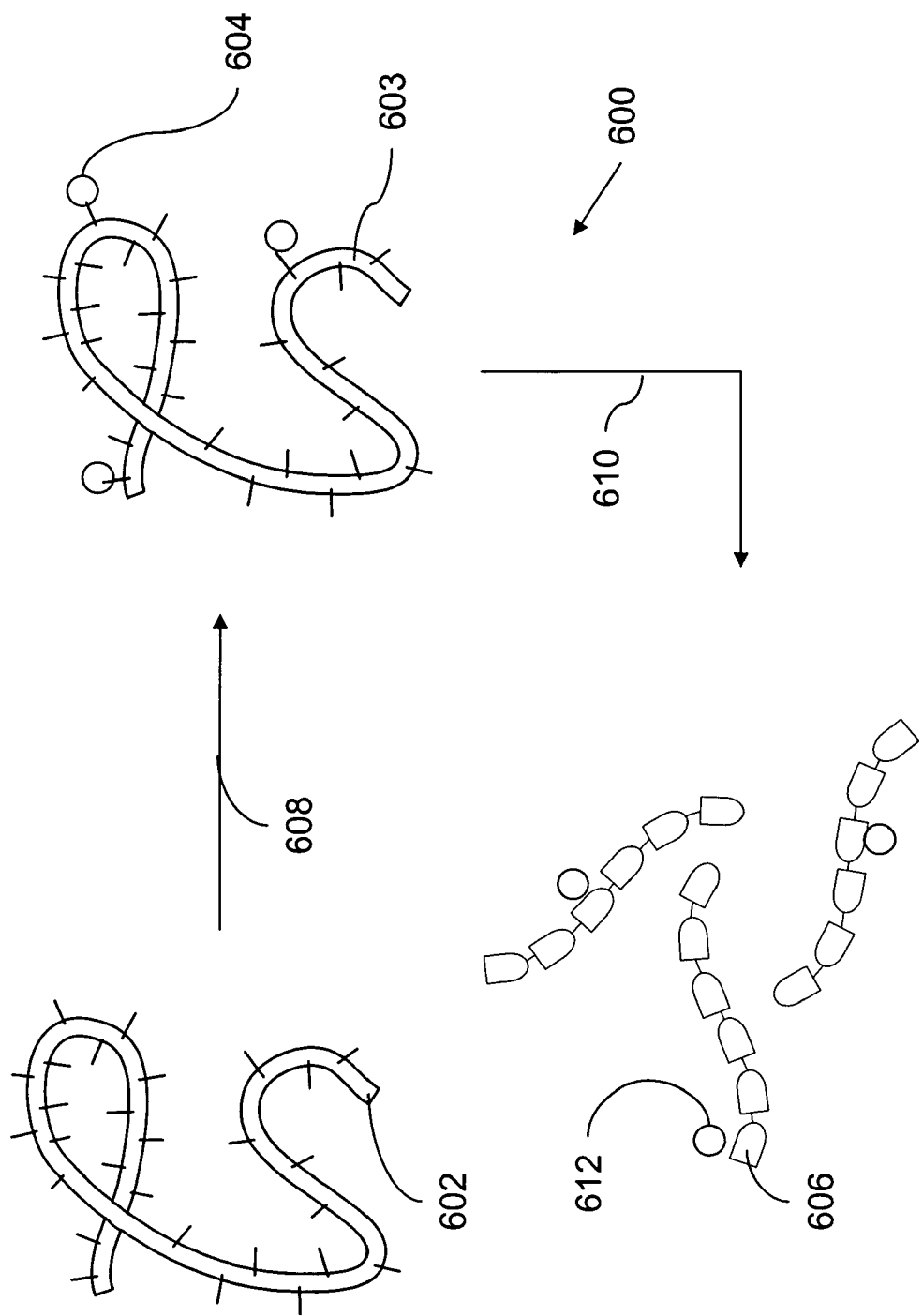
FIG. 6 is a flow diagram of another process of the invention utilizing enzymatic cleavage.

In another embodiment shown in FIG. 6, small proteins themselves are utilized as substrates of pepsin (bovine serum albumen for example). Reference may be had to process 600 depicted in FIG. 6. In the embodiment depicted in FIG. 6, protein 602 contains many pepsin cleavage sites. In step 608 of the process 600, protein 602 is labeled using tags 604. In step 610, labeled protein 603 is exposed to a solution which contains active pepsin. Active pepsin then cleaves labeled protein 603 which produces protein fragments 606, complete with liberated tags 612. The analytical techniques discussed elsewhere in this specification are then utilized to detect protein fragments 606. The concentration of pepsin is then related to the number of protein fragments 606, as compared to the number of labeled proteins 603 which were uncleaved.

Suitable tags include any compound which undergoes a detectable chemical change. For example, azo compounds are easily formed and produce brightly colored compounds. Typical reactions involve utilizing commercially available diazonium salts and various substituted phenols or naphthols. The range of colors generated from such reactions often vary from yellow to orange to red to purple depending on the functionality and substitution patterns of both the diazonium and the phenol/naphthol.

Equation 1:

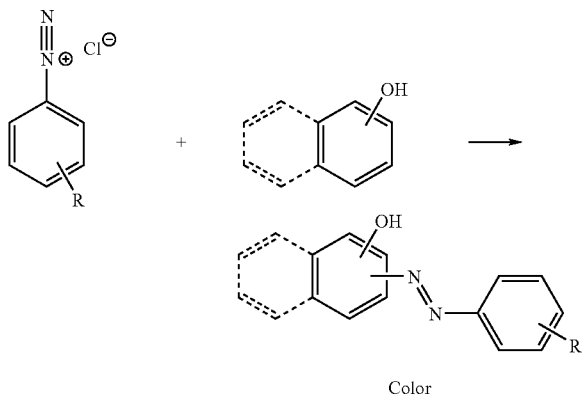

Aromatic alcohols are known to undergo reactions with diazonium salts to form colorful azo compounds. For example, naphthol reacts with Fast Red (a commercially available diazonium salt) to generate a bright red color.

Equation 2:

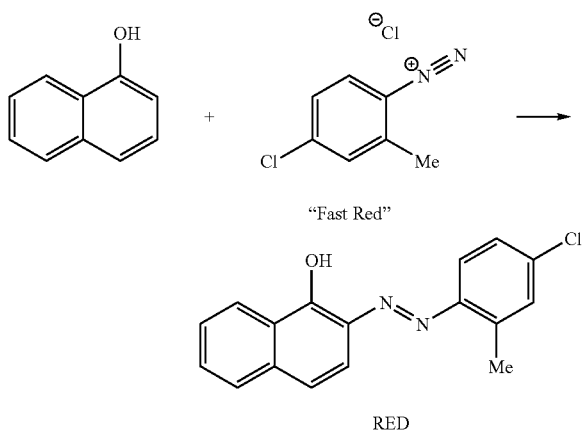

In one embodiment of the invention, this technique is adapted to detect active pepsin. In one such embodiment, the phenol or naphthol is attached to the terminus of a desired amino acid sequence containing aromatic residues. In the presence of pepsin the amide bond of the aromatic amino acid is then hydrolyzed and the arene is released from the solid support and thereafter resides in solution. Reference may be had to equation 3. A diazonium salt is then added to the solution and the salt and phenol/naphthol react and generate the colorful azo compound.

Equation 3: One tag of the present invention

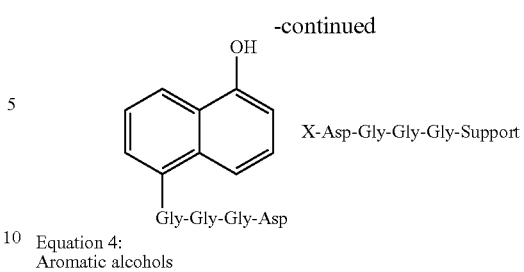

Equation 4:
Aromatic alcohols

Substituted phenols        Substituted naphthols

Aromatic diazonium salt

As will be appreciated by those skilled in the art, phenols are aromatic alcohols that have a single aromatic ring. Naphthols are aromatic alcohols which have two aromatic rings. Diazonium salts are compounds of the general formula $RN_2X$ where X is an anion. It is preferred to use an aromatic diazonium salt in conjunction with the instant invention. The anion X may be a halide (Fast Red), an organic sulfoxide (Fast Red B), and the like.

The proteins or peptides discussed in this application could be easily attached to a strip, solid support or other substrate via standard chemical techniques. In one embodiment an imine is formed at the N-terminal domain of either a protein or peptide using an aldehyde functionalized support. In another embodiment an imine is formed using glutaric dialdehyde in conjunction with an amine functionalized support. One skilled in the art will appreciate that some imine formations are reversible under certain conditions. A variety of techniques have been developed to prevent such reversible reactions. For example, one such technique involes the further modification of the imine via chemical reduction (using sodium cyanoborohydride or sodium borohydride, etc) to yield amines, which are non-reversible products.

In another embodiment, the attachment to the support is via activation of carboxylic acids (either C-terminal acid group or acid groups contained within the peptide or protein side chains). Carboxylic acids can be activated via many different methods, but the most common (and "protein friendly") are activation with DIC (diisopropylcarbodiimide), DCC (dicyclohexylcarbodiimide), DMAP (dimethylaminopyridine), HOBt (hydroxybenzotriazole), to name a few. Attachment using this method would be facilitated via an amine functionalized support.

In yet another embodiment, attachment to the support is achieved using CDI (carbonyl diimidazole). This reacts with free amines on the substrate followed by exposure to the protein or peptide. The activated support is then treated with free amines contained within the substrate to be immobilized; either a protein or peptide.

It will be apparent to one skilled in the art that a variety of other suitable techniques for the attachment of proteins or peptides to solid surfaces are known. The aforementioned examples are intended to be illustrative, and not limiting.

As illustrated in FIG. 7, samples may be obtained by conventional means. For example, samples may be obtained passively (i.e. the patient produces the sample). For example, saliva may be obtained, vigorous coughing may provide sputum (see FIG. 7C), or esophageal secretion may be obtained. Reference may be had to U.S. Pat. No. 5,372,126 to Blau (Pulmonary Sampling Chamber); U.S. patent application 2004/0029205 to Small (Diagnostic System for Differentiating Sputum from Saliva), and the like. Samples may also be obtained actively (i.e. medical personal assists in obtaining the sample). In one embodiment, the oral cavity is swabbed to obtain a sample (see FIG. 7B). Reference may be had to U.S. Pat. No. 4,795,421 to Blasius (Oral Hygiene Swab); U.S. Pat. No. 5,056,521 to Parsons (Method for Monitoring Glucose Level); U.S. Pat. No. 5,975,897 to Propp (Oral Suctioning Swab); and the like. In another embodiment, a device, such as a catheter is passed into the esophagus or upper airway through the nose or mouth to collect the sample (see FIG. 7A). In one such embodiment, a nasoesophageal tube is used to collect the esophageal specimen. In another embodiment, a catheter is attached to, or passed along side of an endoscope (i.e. bronchoscope) to collect the sample. In yet another embodiment, the sample is collected through routine esophagoscopy or bronchoscopy (i.e. by suctioning the sample out of the lung or esophagus). Reference may be had to U.S. Pat. No. 4,880,015 to Nierman (Biopsy Forceps); U.S. Pat. No. 4,702,260 to Wang (Flexible Bronchoscopic Needle Assembly); and the like. The content of U.S. Pat. Nos. 4,702,260; 4,795,421; 4,880,015; 5,056,521; 5,372,126; 5,975,897; and U.S. patent application 2004/0029205 is hereby incorporated by reference into this specification. Many other suitable techniques would likewise be apparent to one skilled in the art.

As used in this specification, the term "solid support" refers to an immobile support such as, for example, a test strip, a wall of a test tube or similar container, an Eppendorf tube, and the like. A variety of suitable solid supports are readily available. Reference may be had to U.S. Pat. Nos. 4,748,114; 5,797,693; 6,441,898; 6,458,596; 6,525,549; U.S. patent application 2004/0002168 and the like. The content of each of these patents is hereby incorporated by reference into this specification. In one embodiment, the test strip is rectangular. In one embodiment, the test strip is comprised of cellulose fibers. In another embodiment, the test strip is cylindrical.

As used in this specification, the term "peptide chain" refers to a chain of amino acids, peptides, proteins, or similar biomolecules, which can be cleaved by an enzyme, and pepsin in particular. Suitable peptides chains are known to those skilled in the art.

As used in this specification, the term "first tag" refers to a chemical moiety placed at one terminus of a peptide chain for later reaction with a second tag. Suitable first tags are likewise known in the art. Examples of suitable first tags include aromatic alcohols, such as substituted phenols, naphthols, and the like.

As used in this specification, the term "chemical dye" refers to a compound capable of staining severed peptide chains. Suitable compounds include, for example, Coomassie brilliant blue, Texas Red, pyrene, fluoroscein, and the like) that is in conjugation with a reactive group, usually an amine.

In one such embodiment the dye contains an aldehyde, for example, or an activated ester (as described previously) and is attached via a free amine present on the peptide or protein. The aforementioned dyes are readily available from commercial sources (Aldrich Chemical) and receive wide usage in chromatography arts.

As used in this specification, the term "second tag" refers to a chemical moiety which undergoes a chemical reaction with a first tag to generate a detectable complex. Suitable second tags are also available. In one embodiment, a second tag undergoes a chemical reaction with the cleaved peptide chain, rather than the first tag (i.e. a peptide stain such as Coomassie Blue). Examples include the aforementioned azo compounds.

As used in this specification, the term "antibody" refers to any immunoglobulin that binds specifically to an antigenic determinant. The term "non-antibody" therefore refers to a material which is not an antibody. Reference may be had to U.S. patent application 2004/0002168.

It is, therefore, apparent that there has been provided, in accordance with the present invention, a method and apparatus for the detection of pepsin. While this invention has been described in conjunction with preferred embodiments thereof, it is evident that many alternatives, modifications, and variations will be apparent to those skilled in the art. Alternative enzymes, other than pepsin, are clearly detectable using the techniques taught in the instant disclosure. Accordingly, it is intended to embrace all such alternatives, modifications and variations that fall within the spirit and broad scope of the appended claims.

We claim:

1. An article for detecting the presence of pepsin suitable to test a subject in a physician's office, the subject suspected of suffering from gastroesophageal reflux disease and providing a sample suspected of containing pepsin, the article comprising:
   a. a solid support comprising a test area surface;
   b. a multiplicity of peptide chains each having a peptide proximal end and a peptide distal end,
   wherein the peptide distal end comprises a peptide bearing a first tag that interacts with a second tag to provide a detectable chromophoric product,
   wherein all of said peptide proximal ends are attached to said test area surface of said support, and
   wherein said peptide chains are cleavable by said pepsin to provide said peptide proximal end attached to said test area surface and said peptide distal end bearing the detectable first tag cleaved from said test area surface.

2. The article as recited in claim 1, wherein said solid support is a test strip.

3. The article as recited in claim 2, wherein said test strip comprises a distal end and a proximal end, and wherein said test area surface is disposed proximate to said distal end.

4. The article as recited in claim 1, wherein said solid support is a tube.

5. The article as recited in claim 4, wherein said tube is a glass tube.

6. The article as recited in claim 4, wherein said tube is an Eppendorf tube.

7. The article as recited in claim 1, wherein said detectable first tag comprises an aromatic alcohol.

8. The article as recited in claim 1, wherein each of said peptide chains comprises an aromatic amino acid.

9. The article as recited in claim 1, wherein said peptide chains comprise an amino acid residue joined by a peptide bond cleavable by said pepsin.

10. The article as recited in claim 9 wherein said amino acid residue is selected from the group consisting of phenylalanine, tyrosine, tryptophan, and histidine.

11. The article described in claim 10 wherein said amino acid residue is preceded by an asparagine residue and followed by an asparagine residue.

12. The article described in claim 1 wherein the peptide chain comprises the sequence —Y—X—Y—, wherein each Y is independently any amino acid residue other than valine, alanine, or glycine, and X is an aromatic amino acid.

13. The article described in claim 12 wherein X is selected from the group consisting of phenylalanine, tyrosine, tryptophan, and histidine.

14. The article described in claim 12 wherein each Y is asparagine.

15. The article described in claim 1 wherein the article detects the presence of pepsin in about 2 hours or less.

16. The article described in claim 1 wherein the second tag comprises an aromatic diazonium salt.

17. The article described in claim 1 wherein the chromophoric product is detectable by the human eye, thereby permitting visual detection of pepsin.

18. The article described in claim 1 further comprising means for obtaining said sample of material.

19. The article described in claim 18 wherein said means for obtaining said sample of material comprises a catheter.

20. An apparatus for detecting the presence of pepsin in a sample of material suitable to test a subject in a physician's office, the subject suspected of suffering from gastroesophageal reflux disease and providing the sample, said apparatus comprising:
   a. an article for exposure to said sample of material, said article comprising a substrate having a test area surface and a multiplicity of peptide chains each having a peptide proximal end and a peptide distal end,
      wherein the peptide distal end comprises a peptide bearing a detectable first tag,
      wherein all of said peptide proximal ends are attached to said test area surface of said substrate, and
      wherein said peptide chains are cleavable by said pepsin to provide said peptide proximal end attached to said test area surface and said peptide distal end bearing the detectable first tag cleaved from said test area surface; and
   b. a container comprising a fillable volume for receiving a test solution comprising at least one of the sample, a buffer and a second tag that interacts with the first tag to provide a detectable chromophoric product, and wherein at least the test area of said article is insertable in said fillable volume.

21. The apparatus as recited in claim 20, wherein said substrate and said container are unitary.

22. The apparatus as recited in claim 21, wherein said container is a tube.

23. The apparatus as recited in claim 22, wherein said tube is a glass tube or an Eppendorf tube.

24. The apparatus as recited in claim 20, wherein said substrate is a test strip.

25. The apparatus as recited in claim 24, wherein said test strip comprises a strip distal end and a strip proximal end, and wherein said test area surface is disposed proximate to said distal end.

26. The apparatus as recited in claim 24, wherein said test strip comprises cellulose fibers.

27. The apparatus as recited in claim 20, wherein said detectable first tag comprises an aromatic alcohol.

28. The apparatus as recited in claim 20, further comprising the test solution disposed in the fillable volume.

29. The apparatus as recited in claim 28, wherein said test solution comprises the second tag.

30. The apparatus as recited in claim 29, wherein said second tag is a chemical dye.

31. The apparatus as recited in claim 28, wherein said test solution comprises a buffer.

32. The apparatus as recited in claim 28, wherein said test solution comprises an aromatic diazonium salt.

33. The apparatus as recited in claim 20, further comprising a test solution disposed in said fillable volume of said container.

34. The apparatus as recited in claim 20, further comprising means for obtaining said sample of material.

35. The apparatus as recited in claim 34, wherein said means for obtaining said sample of material comprises a catheter.

36. The apparatus described in claim 20 wherein the peptide chain comprises the sequence —Y—X—Y—, wherein each Y is independently any amino acid residue other than valine, alanine, or glycine, and X is an aromatic amino acid.

37. The apparatus described in claim 36 wherein X is selected from the group consisting of phenylalanine, tyrosine, tryptophan, and histidine.

38. The apparatus described in claim 36 wherein each Y is asparagine.

39. The apparatus described in claim 20 wherein the apparatus detects the presence of pepsin in a sample of material in about 2 hours or less.

40. The apparatus described in claim 20 wherein the chromophoric product is detectable by the human eye, thereby permitting visual detection of pepsin.

41. The apparatus described in claim 20 wherein each of said peptide chains comprises an aromatic amino acid.

42. The apparatus described in claim 20 wherein said peptide chains comprise an amino acid residue joined by a peptide bond cleavable by said pepsin.

43. The apparatus described in claim 42 wherein said amino acid residue is selected from the group consisting of phenylalanine, tyrosine, tryptophan, and histidine.

44. The apparatus described in claim 43 wherein said amino acid residue is preceded by an asparagine residue and followed by an asparagine residue.

* * * * *